United States Patent [19]

Tóth et al.

[11] 4,221,739
[45] Sep. 9, 1980

[54] AMINO-SUBSTITUTED NITROBENZOPHENONE DERIVATIVES WITH ALKYL, PHENYL, PHENYL ALKYL OR CYCLOALKYL AMINO-SUBSTITUTING GROUPS

[75] Inventors: Edit Tóth; Jozsef Törley; Éva Pálosi; Szábólos Szeberényi; Laszlo Szporny; Sandor Görög; Csilla Mészáros, all of Budapest, Hungary

[73] Assignee: Richter Gedeon Vegyeszeti Gyar R.T., Budapest, Hungary

[21] Appl. No.: 603,853

[22] Filed: Aug. 12, 1975

Related U.S. Application Data

[62] Division of Ser. No. 485,701, Jul. 3, 1974, Pat. No. 3,957,777.

[30] Foreign Application Priority Data

Jul. 26, 1973 [HU] Hungary .................. RI 517

[51] Int. Cl.² .......................................... C07C 97/10
[52] U.S. Cl. ........................................ 260/570 AB
[58] Field of Search ............... 260/570 AB, 501.18

[56] References Cited

U.S. PATENT DOCUMENTS

| | | | |
|---|---|---|---|
| 3,439,016 | 4/1969 | Fryer et al. ............... | 260/570 X |
| 3,449,425 | 6/1969 | Reich et al. ............... | 260/570 |
| 3,510,517 | 5/1970 | Richtes et al. ............. | 260/570 |
| 3,644,528 | 2/1972 | Brown et al. .............. | 260/570 X |

FOREIGN PATENT DOCUMENTS 1062950  12/1963  United Kingdom .................. 260/570

OTHER PUBLICATIONS

"Beilsteins Handbuch Der Organischon Chemie", Band 4, vol. XIII/XIV, p. 390 (1933).

*Primary Examiner*—Robert V. Hines
*Attorney, Agent, or Firm*—Karl F. Ross

[57] ABSTRACT

Compounds of the formula (I),

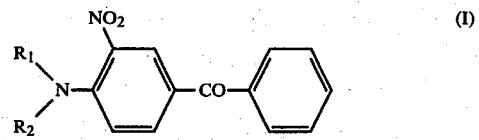

wherein $R_1$ and $R_2$ each is saturated or unsaturated, straight-chained or branched alkyl phenyl, alkylphenyl or saturated or unsaturated cycloalkyl;

but when $R_1$ is methyl, $R_2$ is a group other than methyl, are prepared by reacting a compound of the formula (II),

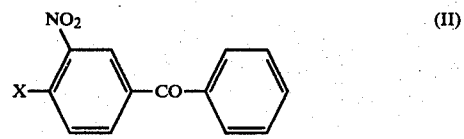

wherein X is halogen, with a secondary amine of the formula (III),

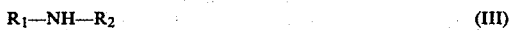

The new compounds of the formula (I), as well as their pharmaceutically acceptable acid addition salts are active primarily in the induction of liver microsomal enzyme, but also possess antipyretic activity.

7 Claims, No Drawings

AMINO-SUBSTITUTED NITROBENZOPHENONE DERIVATIVES WITH ALKYL, PHENYL, PHENYL ALKYL OR CYCLOALKYL AMINO-SUBSTITUTING GROUPS

This is a division of application Ser. No. 485,701, filed July 3, 1974 and now U.S. Pat. No. 3,957,777.

This invention relates to new benzophenone derivatives containing a 3-nitro-4-tert.-amino group, and to acid addition salts thereof.

The compounds according to the invention correspond to the formula (I),

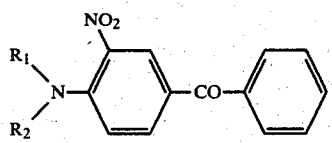

wherein
$R_1$ and $R_2$ each is a saturated or unsaturated, straight-chain or branched alkyl phenyl or alkylphenyl or, saturated or unsaturated cycloalkyl but when $R_1$ is methyl, $R_2$ is a group other than methyl.

$R_1$ or $R_2$ each is preferably saturated or unsaturated, straight-chained or branched $C_{1-18}$ alkyl (e.g. an alkyl, alkenyl, alkynyl or alkadienyl group and), more preferably a $C_{1-10}$ group, such as a methyl, ethyl, propyl, allyl, butyl, isobutyl, pentyl, isopentyl, hexyl, 1-octen-7-yl, nonyl or decyl group.

The pharmacological tests were carried out as follows:

To investigate the enzyme inductive effect, wistar female rats, each weighing 40 to 50 mg. were treated with pure solvent, or with a dosage of 60 mg./kg. of phenobarbital or the compound to be tested 24 hours after this treatment 40 mg./kg. of hexobarbital were administered intravenously to the animals. The reduction of the elimination period and the liver enzyme induction was expressed as the shortening of the duration of sleeping.

To test the antipyretic effect, a 15% yeast suspension was administered to make rats each weighing 180±10 g. No food was given to the animals; they could consume, however, arbitrary amounts of water. 16 hours after the administration of yeast the body temperature of the animals was taken rectally, and the animals were treated with pyrago in an intravenous dosage of 50 M bact./animal. The compound to be tested was administered orally to the animals; thereafter the change in rectal temperature both for the treated and the control animals was recorded for 5 hours, using an "Elab" type electrothermometer. Phenacetine, used as the reference substance, and the compounds of the invention were administered in dosages of 40 mg./kg. body weight.

The results of the above tests are presented in Tables 1 and 2. In these tables the following abbreviations are used:

$B_2$ = 3-nitro-4-morpholino-benzophenone (See Ser. No. 485,701)
$B_9$ = 3-nitro-4-(N,N-diisobutylamino)-benzophenone (Example 1, infra,)
$B_{11}$ = 3-nitro-4-(N-methyl-piperazino)-benzophenone ethobromide (Ser. No. 485,701)
p.o. = per os
S.E. = standard error Table 1

| Compound | Inductive effect | |
|---|---|---|
| | Dosage p.o. mg./kg. | Mean duration of sleeping ± S.E., minutes |
| Control | — | 19.4 ± 1.88 |
| Phenobarbital | 60 | 14.2 ± 1.88* |
| $B_2$ | 60 | 14.6 ± 1.65* |

*p>0.05 (below a significance level of 5%)

Table 2

| Compound | Antipyretic activity |
|---|---|
| | Decrease of temperature, °C. |
| Phenacetine | −1.1 |
| $B_9$ | −1.0 |
| $B_{11}$ | −1.1 |

The anticonvulsive effect was tested on spasm induced by electroshock, tetracor or strychnine, respectively, the muscle relaxation was examined by the rotarod test, while the sedative effect was tested by determining the amount of sodium barbital which does not cause hypnosis.

Inductive effect: $LD_{50}$ mg./kg. p.o.: phenobarbital: 240.0; $B_2$: 1200.0.

Antipyretic activity: $LD_{50}$ mg./kg. p.o.: phenacetine: 2405; $B_9$: above 3000; $B_{11}$: above 3000.

As appears from the date of Table 1, the inductive effect of compound $B_2$ is the same as that of phenobarbital. Phenobarbital is, however, known to exert significant effects on the central nervous system, which is manifested in the test animals in ataxia, sedatio and anticonvulsive effects. By contrast, compound $B_2$ has no effect on the central nervous system in the dosage utilized.

Compounds $B_9$ and $B_{11}$ are similar in antipyretic activity to phenacetine. The compounds of the invention have, however, more favorable therapeutic indices and exert no harmful effect on the kidneys in the pharmacological tests.

The compounds of the invention can be used as pharmaceuticals, and they also are valuable starting substances for the syntheses of pharmacologically active agents.

The new compounds of the formula (I) are prepared according to the invention by reacting a 3-nitro-benzophenone of the general formula (II)

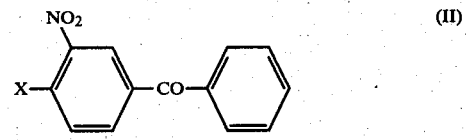

wherein X is halogen, with a secondary amine of the formula (III),

$R_1$—NH—$R_2$.    (III)

If desired, the thus-obtained free bases are converted into their acid addition salts or quaternary ammonium salts, or the free bases are liberated from the compounds in the form of their acid addition salts.

The starting compounds of the formula (II) can be prepared by the method of Maron and Fox (Ber. 2777/1914/).

The reaction is carried out preferably in an organic solvent, in the presence of a base capable of binding the acid liberated in the reaction.

As the solvent, e.g. hydrocarbons (such as gasoline, benzene, or toluene), halogenated hydrocarbons (such as chloroform), ethers (such as dioxane), alcohols (such as ethanol), and esters (such as ethyl acetate), can be used.

As acid binding agent preferably inorganic bases or tertiary organic bases are used. An excess of the amine of the formula (III) may also act as the acid binding agent.

If the amine of the formula (III) or a tertiary organic base used as the hydrogen halide binding agent is applied in excess, it may serve simultaneously as the solvent medium for the reaction.

The reaction is carried out at temperatures ranging from 20° C. to the boiling point of the solvent, preferably at a temperature between 60° C. and 140° C. The progress of the reaction can be monitored easily by thin layer chromatography.

When the reaction has been completed the obtained product is isolated. The reaction mixture can be processed e.g. by pouring the mixture onto water and separating the product by solvent extraction. The organic phase is washed with water until halogen-free; the solution is dried, and the solvent is distilled off. One may also proceed by precipitating the product, filtering, washing with water until halogen-free, and drying. The crude product can be purified by treatment with an appropriate solvent and/or by crystallization.

The new compounds of the formula (I) can be converted into their acid addition salts with mineral or organic acids. The salt-forming acids include hydrochloric acid, hydrobromic acid, sulphuric acid, phosphoric acid, methanesulphonic acid, ethanesulphonic acid, acetic acid, lactic acid, oxalic acid, fumaric acid, maleic acid, tartaric acid, citric acid, succinic acid, amygdalic acid, benzoic acid, salicylic acid and phenylacetic acid.

If desired, the new compounds of the formula (I) can be converted into their quaternary ammonium salts by reacting them with a saturated or unsaturated lower alkylhalide, lower alkylsulphate or benzyl halide.

The acid addition salts and quaternary salts of the compounds of the formula (I) can be converted into the free bases by known methods. The obtained free bases can be converted into other salts, if desired.

The compounds according to the invention are administered to the patients in pharmaceutically active but nontoxic dosages. The actual amount of the active agent to be administered depends on the pharmaceutical effect to be attained, moreover on the method of treatment, as well as on the general condition and sensitivity of the patient to be treated.

The effective dosage can be administered either in subdivided form several times a day, or in (time-release) form.

The pharmacologically active compounds of the invention can be use in therapy in the form of pharmaceutical compositions. Such compositions suitable for enteral, parenteral or topical administration may contain the new compounds according to the invention in admixture with solid or liquid, organic or inorganic, pharmaceutically acceptable carriers which do not react with the active agents. These carriers include water, alcohols, gelatine, propylene glycol, vegetable oils, cholesterol, starch, lactose, talc, gum, magnesium stearate, etc. If desired, the pharmaceutical products can be sterilized.

The pharmaceutical products may contain auxiliary agents, such as preserving, stabilizing, wetting or emulsifying agents, solubilizing substances, salts or buffers to modify the osmotic pressure, etc. These compositions may contain the compounds of the formula (I) in combination with other therapeutically active agents.

The pharmaceutical compositions are prepared by methods well known in the art. Thus, for example, the injectable compositions are prepared by dissolving an acid addition salt or quaternary ammonium salt of the active agent in pyrogen-free physiological saline solution or in bidistilled water, optionally sterilizing the solution, and introducing the composition into ampoules under sterile conditions.

The invention is elucidated in detail in the following Examples.

EXAMPLE 1

3-Nitro-4-(N,N-diisobutylamino)-benzophenone

A mixture of 26 g of 3-nitro-4-chloro-benzophenone, 20 ml. of ethanol and 35 ml. of diisobutylamine is heated to 80° to 85° C. under stirring, and the reaction mixture is kept at this temperature for 6 hours. When the reaction is over, the ethanol is distilled off under reduced pressure, and 260 ml. of petroleum ether (b.p.: 40° to 100° C.) are added to the solid residue. The separated diisobutylamine hydrochloride is removed by filtration, the filtrate is evaporated, and the residue is recrystallized from ethanol. 32.7 g of 3-nitro-4-(N,N-diisobutylamino)-benzophenone are obtained, m.p. 80°–81° C. (compound B9 supra)

Analysis for $C_{21}H_{26}N_2O_3$. Calculated: C 71.16%; H 7.39%; N 7.90%. Found: C 71.34%; H 7.35%; N 7.99%.

I.R. spectrum: characteristic bands appear at 700, 730, 830, 870, 1320, 1525, 1650, 2880, 2920, 2940, and 2960 $cm^{-1}$.

U.V. spectrum: $\lambda_{max.}^{EtOH} = 252, 345, 410$ nm.

EXAMPLE 2

3-Nitro-4-(N,N-di-n-amylamino)-benzophenone

A mixture of 9.12 g. of 3-nitro-4-chloro-benzophenone, 11 g. of di-n-amylamine and 10 ml. of benzene is refluxed for 40 minutes with stirring. The mixture is allowed to cool and diluted with 140 ml. of benzene. The organic base is washed with water until chloride-free. The benzene phase is dried over anhydrous magnesium sulphate, filtered, and evaporated under reduced pressure. 13.3 g. of 3-nitro-4-(N,N-di-n-amylamino)-benzophenone are obtained as a viscous, oily residue.

Analysis for $C_{23}H_{30}N_2O_3$: Calculated: C 72.22%; H 7.91%; H 7.32%. Found: C 72.11%; H 7.72%; H 7.40%.

I.R. spectrum: characteristic bands appear at 700, 740, 800, 870, 1320, 1530, 1650, 2880, 2860, 2940, and 2960 $cm^{-1}$.

U.V. spectrum: $\lambda_{max.}^{EtOH} = 252, 344, 410$ nm.

EXAMPLE 3

3-Nitro-4-(N-ethyl-N-cyclohexylamino)-benzophenone 13 g. of 3-nitro-4-chloro-benzophenone are reacted with 15 ml. of N-ethyl-N-cyclohexylamine as described in Example 2. The crude product is recrystallized from n-hexane to yield 15.3 g of pure, crystalline 3-nitro-4-(N-ethyl-N-cyclohexylamino)-benzophenone; m.p. 91.5°–92° C.

Analysis for $C_{21}H_{24}N_2O_3$: Calculated: C 71.57%; N 6.86%; N 7.95%. Found: C 71.66%; H 6.93%; N 7.82%.

I.R. spectrum: characteristic bands appear at 710, 730, 800, 860, 1310, 1530, 1650, 2860, and 2940 $cm^{-1}$.

U.V. spectrum: $\lambda_{max.}^{EtOH} = 252, 346$ nm.

EXAMPLE 4

3-Nitro-4-(N-methyl-N-octylamino)-benzophenone

A mixture of 9.23 g. of 3-nitro-4-chloro-benzophenone, 10 ml. of ethanol and 10.3 g. of N-methyl-N-octylamine is stirred at 80° to 85° C. for 30 minutes, and then the mixture is poured onto 100 ml. of ice water. The aqueous phase is extracted with 2×75 ml. of benzene. The benzene phases are combined, washed with distilled water until chloride-free, dried over anhydrous magnesium sulphate, filtered, and evaporated in vacuo. 11.57 g. of 3-nitro-4-(N-methyl-N-octylamino)-benzophenone are obtained in the form of an oily residue. On the basis of thin layer chromatographical examination, a pure, uniform product is obtained.

Analysis for $C_{22}H_{28}N_2O_3$: Calculated: C 71.71%; H 7.66%; N 7.60%. Found: C 71.65%; H 7.58%; N 7.66%.

I.R. spectrum: characteristic bands appear at 700, 740, 820, 875, 1320, 1530, 1650, 2850, and 2940 $cm^{-1}$.

U.V. spectrum: $\lambda_{max.}^{EtOH} = 248, 340, 406$ nm.

EXAMPLE 5

3-Nitro-4-(N-ethyl-N-phenylamino)-benzophenone 30.6 g. of 3-nitro-4-bromo-benzophenone are reacted with 23.5 ml. of N-ethylaniline as described in Example 2. The obtained 34 g. of crude 3-nitro-4-(N-ethyl-N-phenyl-amino)-benzophenone are recrystallized from ethanol to yield 27.68 g. of pure, crystalline product, melting at 99.5° C.

Analysis for $C_{21}H_{18}N_2O_3$: Calculated: C 72.82%; H 5.24%; N 8.09%. Found: C 72.91%; H 5.31%; N 8.10%.

I.R. spectrum: characteristic bands appear at 700, 710, 740, 800, 870, 1320, 1530, 1650, 2920, and 2980 $cm^{-1}$.

U.V. spectrum: $\lambda_{max.}^{EtOH} = 252, 352$ nm.

EXAMPLE 6

3-Nitro-4-(N-methyl-N-benzylamino)-benzophenone 26 g. of 3-nitro-4-chloro-benzophenone are reacted with 26.84 ml. of N-methyl-N-benzylamine as described in Example 2. The benzene solution is evaporated, and the residue is suspended in n-hexane. The solids are filtered off and dried to yield 32.9 g. of 3-nitro-4-(N-methyl-N-benzylamino)-benzophenone; m.p.: 99.5° C.

Analysis for $C_{21}H_{18}N_2O_3$: Calculated: C 72.82%; H 5.24%; N 8.09%. Found: C 72.94%; H 5.16%; N 7.99%.

What we claim is:

1. A compound of the formula:

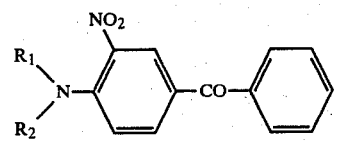

and pharmaceutically acceptable acid addition salts thereof, wherein $R_1$ and $R_2$ are each a saturated or unsaturated straight or branched $C_1$ to $C_{18}$ alkyl, a phenyl-$C_1$ to $C_4$ alkyl, a saturated or unsaturated $C_3$ to $C_8$ cycloalkyl, phenyl, halophenyl, $C_1$ to $C_4$ alkylphenyl, or alkoxyphenyl, with the proviso that if $R_1$ is methyl, $R_2$ is not methyl.

2. The compound defined in claim 1 which consists of 3-nitro-4-(N,N-diisobutylamino)-benzophenone, and pharmaceutically acceptable acid addition salts thereof.

3. The compound defined in claim 1 which consists of 3-nitro-4-(N,N-di-n-amylamino)-benzophenone, and pharamceutically acceptable acid addition salts thereof.

4. The compound defined in claim 1 which consists of 3-nitro-4-(N-ethyl-N-cyclohexylamino)-benzophenone, and pharmaceutically acceptable acid addition salts thereof.

5. The compound defined in claim 1 which consists of 3-nitro-4-(N-methyl-N-octylamino)-benzophenone, and pharmaceutically acceptable acid addition salts thereof.

6. The compound defined in claim 1 which consists of 3-nitro-4-(N-ethyl-N-phenylamino)-benzophenone, and pharmaceutically acceptable acid addition salts thereof.

7. The compound defined in claim 1 which consists of 3-nitro-4-(N-methyl-N-benzylamino)-benzophenone, and pharmaceutically acceptable acid addition salts thereof.

* * * * *